US010863290B1

(12) United States Patent
Ayache (10) Patent No.: US 10,863,290 B1
(45) Date of Patent: Dec. 8, 2020

(54) CHARGING AND DRYING STATION FOR HEARING AID DEVICE

(71) Applicant: Jamal M. Ayache, Irvine, CA (US)

(72) Inventor: Jamal M. Ayache, Irvine, CA (US)

( * ) Notice: Subject to any disclaimer, the term of this patent is extended or adjusted under 35 U.S.C. 154(b) by 0 days.

(21) Appl. No.: 16/945,432

(22) Filed: Jul. 31, 2020

Related U.S. Application Data

(63) Continuation-in-part of application No. 16/097,613, filed as application No. PCT/US2018/036776 on Jun. 8, 2018.

(51) Int. Cl.
| | | |
|---|---|---|
| *H04R 25/00* | (2006.01) | |
| *H04R 1/12* | (2006.01) | |
| *H02J 7/00* | (2006.01) | |
| *H05K 7/14* | (2006.01) | |
| *A61L 2/10* | (2006.01) | |
| *F26B 3/20* | (2006.01) | |
| *A61L 2/26* | (2006.01) | |

(52) U.S. Cl.
CPC ............... *H04R 25/60* (2013.01); *A61L 2/10* (2013.01); *A61L 2/26* (2013.01); *F26B 3/20* (2013.01); *H02J 7/0044* (2013.01); *H04R 1/12* (2013.01); *H04R 25/55* (2013.01); *H04R 25/602* (2013.01); *H05K 7/1427* (2013.01); *A61L 2202/11* (2013.01); *A61L 2202/121* (2013.01); *A61L 2202/122* (2013.01); *H04R 2225/31* (2013.01); *H04R 2460/17* (2013.01)

(58) Field of Classification Search
CPC ........ H04R 1/1025; H04R 1/12; H04R 25/60; H04R 25/602; H04R 2225/021; H04R 2225/31; H04R 2225/33; H04R 2460/17; H04J 7/0044

USPC ......... 381/322, 323, 324, 328, 330; 320/107
See application file for complete search history.

(56) References Cited

U.S. PATENT DOCUMENTS

| | | | | |
|---|---|---|---|---|
| 6,399,920 | B1* | 6/2002 | Guinn ..................... | F26B 9/003 219/386 |
| 7,017,276 | B2* | 3/2006 | Greenspan .............. | F26B 9/003 34/201 |
| 2009/0074219 | A1* | 3/2009 | Klemenz ................ | H04R 25/00 381/324 |
| 2009/0296968 | A1* | 12/2009 | Wu ........................ | H04R 25/00 381/323 |
| 2012/0216418 | A1* | 8/2012 | Serman ................... | F26B 9/003 34/282 |
| 2016/0277848 | A1* | 9/2016 | Naumann .............. | H04R 25/30 |

* cited by examiner

*Primary Examiner* — Huyen D Le
(74) *Attorney, Agent, or Firm* — Tsz Lung Yeung (57) ABSTRACT

A charging and drying station for a hearing aid device includes a hearing aid charger, a main casing, and a drying arrangement. The main casing has a drying platform, a charger accommodating cavity, a supporting compartment and a drying compartment. The drying arrangement includes a thermal dryer provided in the supporting compartment for generating heat in the drying platform. The hearing aid charging is detachably attached on the main casing in the charger accommodating cavity so that the housing of the hearing aid device is capable of being disposed on the hearing aid charger while the earplug of the hearing aid device is arranged to be disposed on the drying platform so as to allow the hearing aid device is capable of being simultaneously recharged and dried by the hearing aid charger and the drying arrangement respectively.

15 Claims, 12 Drawing Sheets

CHARGING AND DRYING STATION FOR HEARING AID DEVICE

CROSS REFERENCE TO RELATED APPLICATION

This is a Continuation-in-part of a non-provisional application having an application number of 16/097,613, a filing date of Oct. 29, 2018. This non-provisional application is a national phase of PCT application having an application number of PCT/US18/36776 and a filing date of Jun. 8, 2018.

BACKGROUND OF THE PRESENT INVENTION

Field of Invention

The present invention relates to a hearing aid accessory, and more particularly to a charging and drying station for a hearing aid device, wherein a user may simultaneously recharge and dry his hearing aid device through the use of an existing hearing aid charger and the present invention.

Description of Related Arts

Hearing aids have been widely utilized throughout the world. A typical behind-the-ear hearing aid may comprise a housing which is adapted to be hung behind a user's pinna, and an earplug extended from the housing and arranged to be inserted into an external auditory canal of the user. The hearing aid may comprise a speaker/receiver and microphone module which is normally received in the housing. A rechargeable battery may be provided in the housing for powering up the entire hearing aid. An electrical terminal may be provided on the housing.

Two common hearing aid accessories are chargers and dryers. Hearing aid chargers are used to recharge the rechargeable battery while dryers may be used to remove moisture from the hearing aids. Conventionally, recharging and drying are two separate processes and a user has to use two different accessories to accomplish charging and drying. This imparts great inconvenient to users.

As a result, there is a need to develop an accessory for a hearing aid device which may resolve the above-mentioned problem and allow a user to charge and dry his hearing aid devices at the same time.

SUMMARY OF THE PRESENT INVENTION

Certain variations of the present invention provide a charging and drying station for a hearing aid device, wherein a user may simultaneously recharge and dry his hearing aid device through the use of an existing hearing aid charger and the present invention.

Certain variations of the present invention provide a charging and drying station for a hearing aid device, wherein a user may store the hearing aid device in a main casing which is designed to be of portable use. In other words, the present invention may provide a portable charging station when the hearing aid charger is accommodated in the charging and drying station.

Certain variations of the present invention provide a charging and drying station for a hearing aid device, wherein a user may simultaneously recharge and dry his hearing aid device through the use of a provided hearing aid charger of the present invention.

In one aspect of the present invention, it provides a charging and drying station for a hearing aid charger having a charging terminal to charge a hearing aid device which comprises a housing and an earplug, the charging and drying station comprising:

a main casing having a receiving cavity; and a drying arrangement accommodated in the receiving cavity, the drying arrangement comprising a supporting tray and a thermal dryer mounted in the receiving cavity for drying the hearing aid device, the supporting tray being provided on the through dryer slot for supporting at least the earplug of the hearing aid, wherein when the hearing aid charger is detachably accommodated in the receiving cavity, the housing of the hearing aid device is capable of being connected to the hearing aid charger while the earplug of the hearing aid device being arranged to be disposed on the supporting tray for being simultaneously recharged and dried by the hearing aid charger and the drying arrangement respectively.

In another aspect of the present invention, it provides a charging and drying station for a hearing aid charger having a charging terminal to charge a hearing aid device which comprises a housing, an earplug and an extension cord connecting the housing and the earplug, the charging and drying station comprising:

a main casing having a receiving cavity and a charger accommodating cavity, the main casing further comprising a drying platform provided in the receiving cavity to divide the receiving cavity into a supporting compartment and a drying compartment on underneath and above the drying platform respectively; and a drying arrangement, which comprises a thermal dryer provided in the supporting compartment of the receiving cavity for generating heat in the drying platform, wherein the charger accommodating cavity is shaped and sized to fittedly accommodate the hearing aid charger in a detachable manner, so that the housing of the hearing aid device is capable of being disposed on the hearing aid charger while the earplug of the hearing aid device is arranged to be disposed on the drying platform so that the hearing aid device is simultaneously recharged and dried by the hearing aid charger and the drying arrangement respectively.

In another aspect of the present invention, it provides a charging and drying station for a hearing aid device which comprises a housing, an earplug and an extension cord connecting the housing and the earplug, the charging and drying station comprising:

a hearing aid charger which comprises a charger body, at least one charging adapter provided on the charger body, at least one charging terminal provided on the charging adapter, and a rechargeable battery provided in the charger body and electrically connected to the charging terminal;

a main casing having a receiving cavity and a charger accommodating cavity, the main casing further comprising a drying platform provided in the receiving cavity to divide the receiving cavity into a supporting compartment and a drying compartment on underneath and above the drying platform respectively, the charger accommodating cavity being shaped and sized to fittedly accommodate the hearing aid charger; and a drying arrangement which comprises a thermal dryer provided in the supporting compartment of the receiving cavity for generating heat in the drying platform, the hearing aid charging being detachably attached on the main casing in the charger accommodating cavity, so that the housing of the hearing aid device is capable of being disposed on the hearing aid charger while the earplug of the hearing aid device is arranged to be disposed on the drying platform so as to allow the hearing aid device is capable of being simultaneously recharged and dried by the hearing aid charger and the drying arrangement respectively.

This summary presented above is provided merely to introduce certain concepts and not to identify any key or essential features of the claimed subject matter.

DETAILED DESCRIPTION OF THE PREFERRED EMBODIMENT

The following detailed description of the preferred embodiments is the preferred mode of carrying out the invention. The description is not to be taken in any limiting sense. It is presented for the purpose of illustrating the general principles of the present invention.

It should be appreciated that the terms "install", "connect", "couple", and "mount" in the following description refer to the connecting relationship in the accompanying drawings for easy understanding of embodiments of the present disclosure. For example, the connection can refer to permanent connection or detachable connection. Furthermore, "connected" may also mean direct connection or indirect connection, or connection through other auxiliary components. Therefore, the above terms should not be an actual connection limitation of the elements of embodiments of the present disclosure.

It should be appreciated that the terms "length", "width", "top", "bottom", "front", "rear", "left", "right", "vertical", "horizontal", "upper", "lower", "exterior", and "interior" in the following description refer to the orientation or positioning relationship in the accompanying drawings for easy understanding of embodiments of the present disclosure without limiting the actual location or orientation of embodiments of the present disclosure. Therefore, the above terms should not be an actual location limitation of the elements of embodiments of the present disclosure.

It should be appreciated that the terms "first", "second", "one", "a", and "an" in the following description refer to "at least one" or "one or more" in the embodiment. In particular, the term "a" in one embodiment may refer to "one" while in another embodiment may refer to "more than one". Therefore, the above terms should not be an actual numerical limitation of the elements of embodiments of the present disclosure.

Referring to FIG. 1 to FIG. 4 of the drawings, a charging and drying station according a first preferred embodiment of the present invention is illustrated. The charging and drying station may be primarily for use with a hearing aid charger 200 having at least one charging terminal 201 to charge at least one hearing aid device 100. Broadly, the charging and dryer station may comprise a main casing 10 having a receiving cavity 11, a drying arrangement 20, and a charger accommodation arrangement 30.

The drying arrangement 20 may be accommodated in the receiving cavity 11. The drying arrangement 20 may comprise at least one of an air dryer 21 and a thermal dryer 22 mounted in the receiving cavity 11 for drying the hearing aid device 100.

The charger accommodation arrangement 30 may comprise a utility platform 31 securely mounted on the main casing 10. The utility platform 31 may have a through charger accommodating slot 311 which may be shaped to fittedly accommodate at least the charging terminal 201 of the hearing aid charger 200 when the hearing aid charger 200 is detachably accommodated in the receiving cavity 11, so that the hearing aid device 100 is capable of being disposed on the utility platform 31 for being simultaneously recharged and dried by the hearing aid charger 200 and the drying arrangement 20 respectively.

According to the first preferred embodiment of the present invention, the charging and drying station may be primarily for use with a predetermined hearing aid charger 200 having at least one charging terminal 201. The hearing aid charger 200 may be a leading hearing aid charger in the market. The size and shape of this hearing aid charger 200 may be utilized to design the size and shape of the receiving cavity 11 and the through charger accommodating slot 311.

Figure 1:
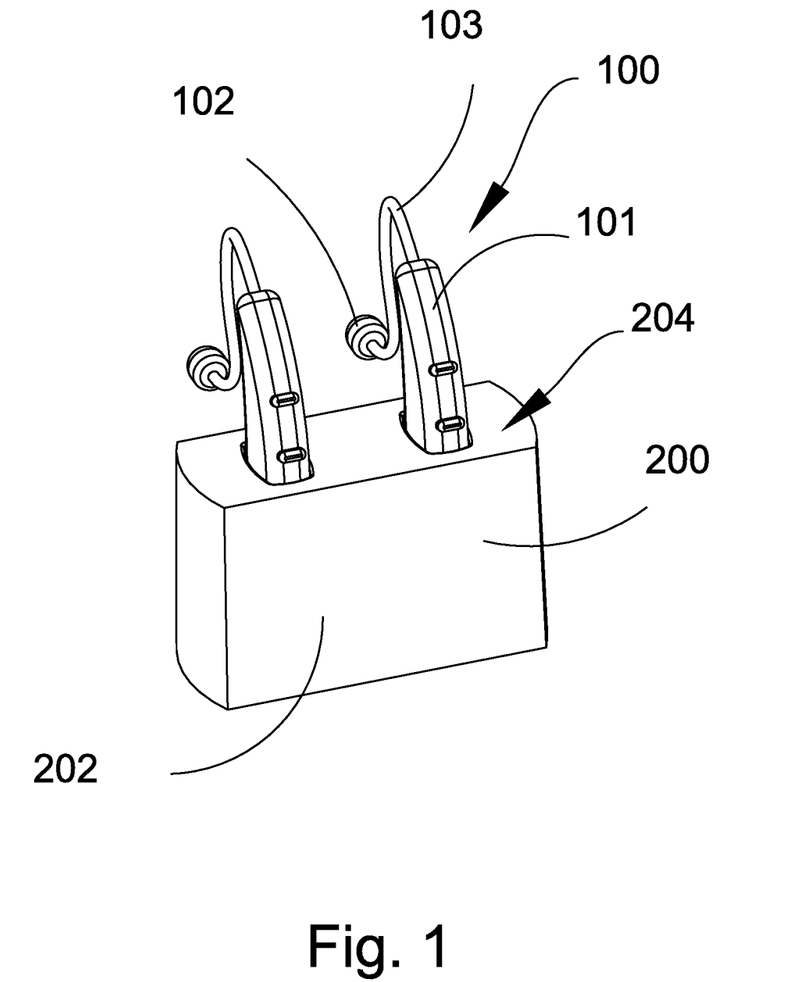
FIG. 1 is a schematic diagram illustrating two hearing aid devices are being charged by a hearing aid charger.

FIG. 1 illustrates charging of two hearing aid devices 100 by a hearing aid charger 200. Each of the hearing aid devices 100 may comprise a housing 101, an earplug 102, and an extension cord 103 extended between the housing 101 and the earplug 102. The earplug 102 and the extension cord 103 may be made of flexible and soft material while the housing 101 may be made of rigid material. Electronic components may be received in the housing 101. The two hearing aid devices 100 may be conventional and well-known in the art.

The hearing aid charger 200 may also be a conventional charger for a hearing aid device. FIG. 1 illustrates one predetermined type of hearing charger in which it may comprise a charger body 202, a plurality of charging adapters 203 provided on a top surface 204 of the charger body 202, wherein each of the charging adapters 203 may have a charging terminal 201 provided thereon. The housings 101 of the hearing aid devices 100 may be securely disposed on the charging adapters 203 respectively for charging of the hearing aid devices 100. Again, the hearing aid charger 200 may be conventional and well-known in the art.

Figure 2:
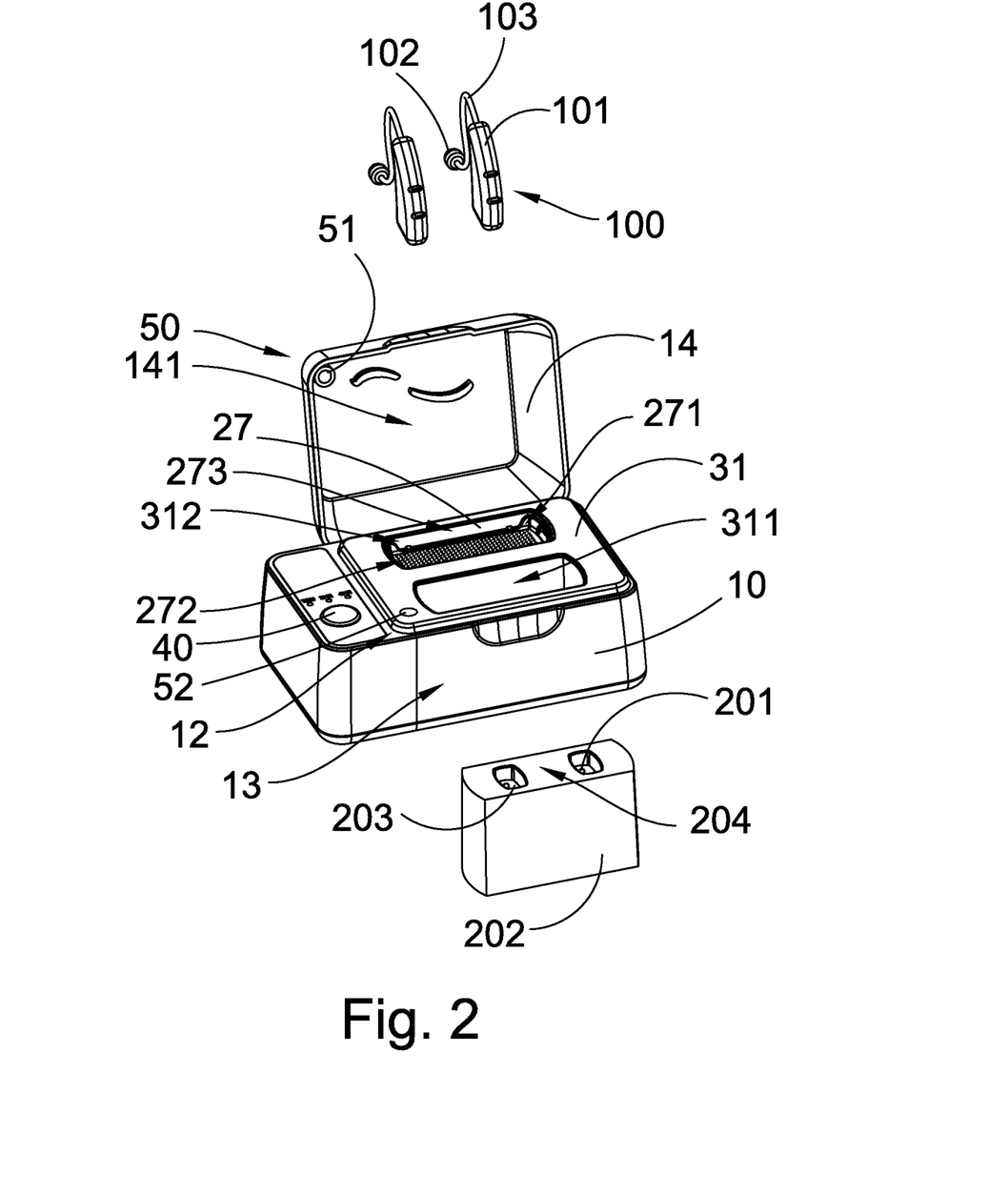
FIG. 2 is a perspective view of the charging and drying station for a hearing aid device according to the first preferred embodiment of the present invention.
Figure 3:
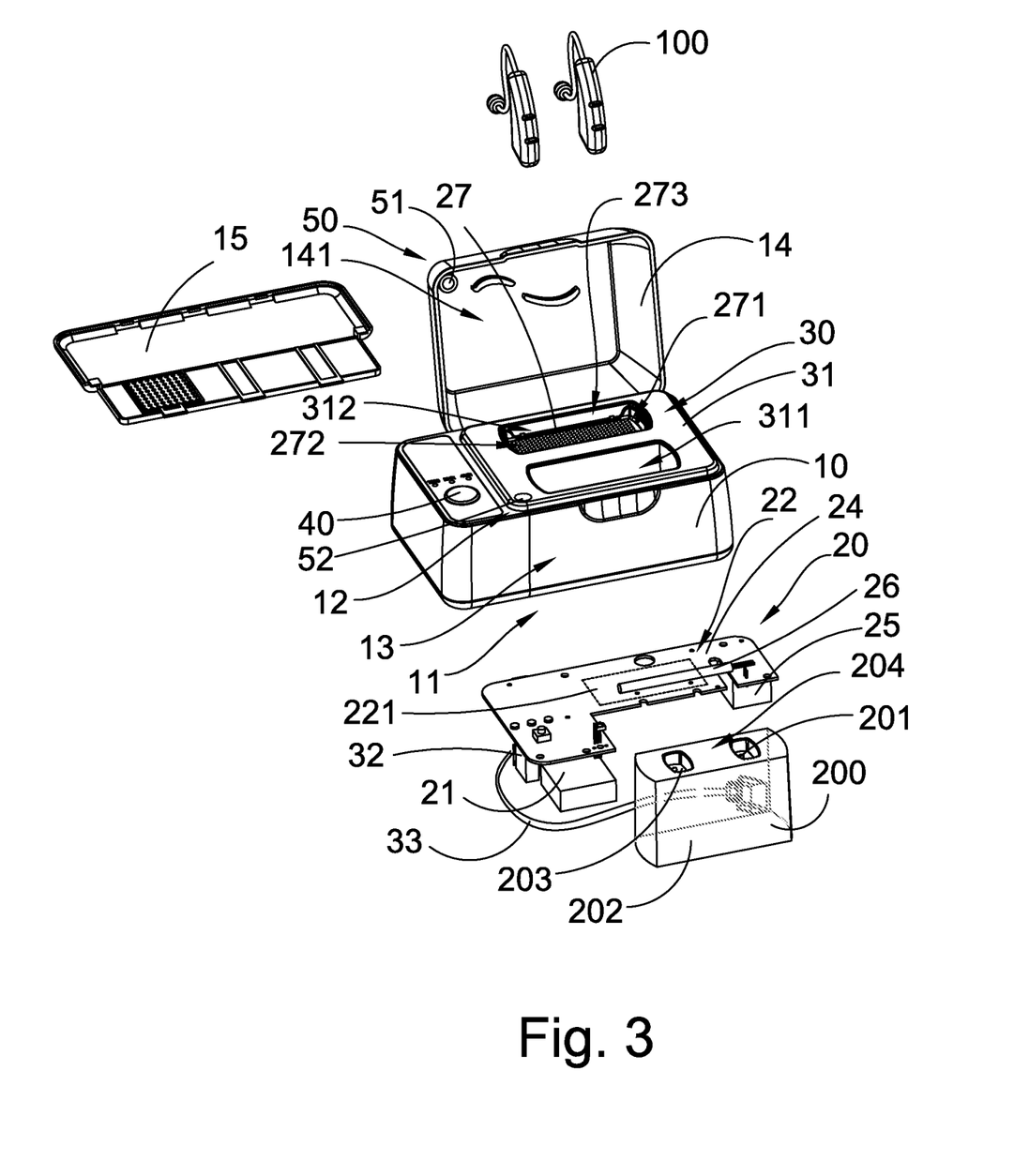
FIG. 3 is exploded perspective view of the charging and drying station for a hearing aid device according to the first preferred embodiment of the present invention.

The main casing 10 may have a top surface 12 and a boundary surface 13. The charging and drying station may further comprise a covering member 14 movably mounted on the main casing 10 for selectively covering the utility platform 31 of the charger accommodation arrangement 30.

On the other hand, the receiving cavity 11 may be formed as a space surrounded between the top surface 12, the utility platform 31, and the boundary surface 13. The receiving cavity 11 may formed as a cavity inside the main casing 10. In this first preferred embodiment, the main casing 10 may have a substantially rectangular cross-sectional shape. However, depending on manufacturing and marketing circumstances, the main casing 10 may also be configured to have any other cross-sectional shape.

The charging and drying station may further comprise a bottom cover 15 detachably attached on a bottom side of the main casing 10. When the bottom cover 15 is detached from the main casing 10, a user may be able to accommodate the hearing aid charger 200 in the receiving cavity 11.

Figure 4:
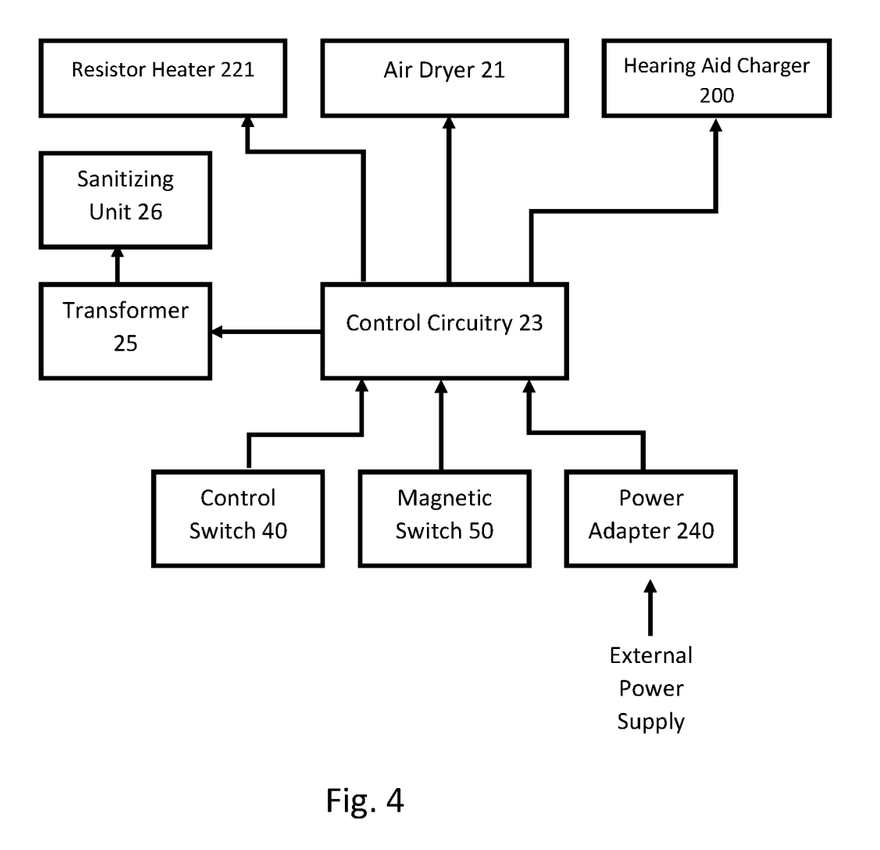
FIG. 4 is a schematic block diagram of the charging and drying station for a hearing aid device according to the first preferred embodiment of the present invention.

The drying arrangement 20 may further comprise a control circuitry 23 implemented on a Printed Circuit Board (PCB 24). The PCB 24 may be securely supported in the receiving cavity 11. The air dryer 21 may be electrically connected to the PCB 24 for being controlled by the control circuitry 23. The control circuitry 23 may serve as a central circuit for controlling all other electrical components of the charging and drying station of the present invention. The PCB 24 may be electrically connected to an external power source, preferably through an externally connected power adapter 240, for acquiring electricity for the entire charging and drying station.

The drying arrangement 20 may further comprise a sanitizing unit 26 provided in the receiving cavity 11 and electrically connected to the PCB 24 and the control circuitry 23 for sanitizing the hearing aid device 100 when it is disposed on the utility platform 31. The sanitizing unit 26 may be configured as an ultra-violet (UV) generator mounted on a top side of the PCB 24 so that when the sanitizing unit 26 is activated, it may be arranged to generate ultra-violet radiation primarily toward the utility platform 31 for sanitizing the hearing aid device 100.

In order to optimize power supply to the sanitizing unit 26, the drying arrangement 20 may further comprise a power transformer 25 supported in the receiving cavity 11 and electrically connected to the PCB 24 and the control circuitry 23. The power transformer 25 may also be electrically connected to the sanitizing unit 26 and arranged to provide electrical power to the sanitizing unit 26. The power transformer 25 may acquire electrical power from the PCB 24, and this available electrical supply on the PCB 24 may be transformed into a predetermined voltage and current for use by the sanitizing unit 26. Thus, when the control circuitry 23 is actuated (described below), the control circuitry 23 may supply power to the air dryer 21, the thermal dryer 22, and sanitizing unit 26 and drive these components to operate accordingly.

The charger accommodation arrangement 30 may be configured to allow a user to dry and charge his hearing aid device 100 simultaneously. The utility platform 31 may further comprise a through dryer slot 312 formed adjacent to the through charger accommodating slot 311, while the drying arrangement 20 may further comprise a supporting tray 27 mounted on the through dryer slot 312. The supporting tray 27 may have a drying cavity 271 indently formed thereon, and a plurality of meshes 272 formed on a surrounding boundary 273 of the drying cavity 271. The drying cavity 271 may be shaped and sized to accommodate at least the earplug 102 of the hearing aid device 100 so that the earplug 102 may rest in the drying cavity 271 for being dried by the drying arrangement 20. Thus, the meshes 272 may communicate the receiving cavity 11 with the drying cavity 271.

According to the first preferred embodiment of the present invention, the drying arrangement 20 may comprise both the air dryer 21 and the thermal dryer 22. The air dryer 21 may be configured as a fan unit which may be arranged to deliver air flow. On the other hand, the thermal dryer 22 may comprise at least one resistor heater 221 mounted on the PCB 24, wherein the air circulated from the air dryer 21 may be arranged to thermally communicate with the resistor heater 221 for being heated. The heated air may then be circulated toward the drying cavity 271 through the meshes 272.

The charger accommodation arrangement 30 may further comprise a power port 32 provided on the PCB 24, and a power cable 33 extended from the power port 32 for electrically connecting to the hearing aid charger 200 so as to supply electricity thereto. Specifically, the power port 32 may be configured as a USB power port and the power cable 33 may connect the hearing aid charger 200 to the power port 32 when the hearing aid charger 200 is accommodated in the receiving cavity 11. The power supplied to the hearing aid charger 200 through the power port 32 may be used to recharge the hearing aid charger 200 for recharging the hearing aid device 100.

In this first preferred embodiment, the through charger accommodating slot 311 of the utility platform 31 may be shaped and sized to accommodate the top surface 204 of the hearing aid charger 200, while the charging adapters 203 are provided on the top surface 204 of the hearing aid charger 200. Thus, when the hearing aid charger 200 is properly accommodated in the receiving cavity 11, the top surface 204 and the charging adapter 203 may expose to an exterior of the receiving cavity 11 through the through charger accommodating slot 311. A user may then charge the hearing aid device 100 by connecting the hearing aid device 100 to the charging adapter 203 while placing the hearing aid device 100 on the utility platform 31.

The covering member 14 may be pivotally mounted to the main casing 10 and may have a covering cavity 141 for accommodating the hearing aid device 100. The covering member 14 may be pivotally moved to expose the drying cavity 271 and the hearing aid device 100 to ambient environment. On the other hand, the covering member 14 may also be pivotally moved to rest on the main casing 10 so as to substantially enclose and protect the hearing aid device 100 and the supporting tray 27.

Moreover, the charging and drying station may further comprise a magnetic switch 50 provided on the main casing 10. Specifically, the magnetic switch 50 may comprise a first magnetic member 51 provided on the covering member 14 and a second magnetic member 52 provided in the receiving cavity 11 and electrically connected to the control circuitry 23 and the PCB 24, in such a manner that when the covering member 14 is moved to enclose the hearing aid device 100, the first magnetic member 51 and the second magnetic member 52 may be magnetically attracted with each other to activate operation of the drying arrangement 20 and/or charging function.

The charging and drying station may further comprise a control switch 40 provided on the main casing 10 and electrically connected to the control circuitry 23, wherein a user may control an operation of the charging and drying station through actuating the control switch 40.

The operation of the present invention is as follows: the charging and drying station of the present invention does not come with a hearing aid charger 200. Rather, the present invention is for accommodating a predetermined hearing aid charger 200 which is adapted to charge a hearing aid device 100. The charging and drying station of the present invention may be sized and shaped to simultaneously dry and charge two hearing aid devices 100. Thus, a user may insert the hearing aid charger 200 in the receiving cavity 11 and connect the power cable 33 to a built-in charging socket of the hearing aid charger 200. After that, the user may close the bottom cover 15 so that the hearing aid charger 200 may be securely supported and accommodated in the receiving cavity 11. At the same time, the charging adapters 203 may expose to ambient environment through the through charger accommodating slot 311.

Referring to FIG. 1 of the drawings, a user may then connect the hearing aid devices 100 to the charging adapters 203 in the through charger accommodating slot 311 while the earplug 102 of each of the hearing aid devices 100 may extend and rest in the drying cavity 271 of the adjacently positioned supporting tray 27 (in the through dryer slot 312). The user may then close the covering member 14 and turn on the air dryer 21 and the thermal dryer 22, and/or the sanitizing unit 26 by operating on the control switch 40. Thus, the hearing aid devices 100 may be recharged and dried simultaneously by using the present invention.

Moreover, the sanitizing unit 26 of the drying arrangement 20 may generate ultraviolet radiation which may reach the hearing aid devices 100 through the meshes 272 of the supporting tray 27. A user of the present invention may choose which functions to be used for one or both of his hearing aid devices 100. For example, the user may activate both the drying and sanitizing functions for both of his hearing aid devices 100 by manually operating on the control switch 40.

Note that the charging and drying station of the present invention may be built for many types of hearing aid chargers. By altering the size and shape of the through charger accommodating slot 311 and by suitably programming the control circuitry 23, the present invention may be used in conjunction with many commercially available hearing aid chargers.

The control circuitry 23 may be configured to recharge the hearing aid charger 200 when it is accommodated in the receiving cavity 11 and electrically connected to the control circuitry 23 through the power port 32. The control circuitry 23 may acquire the necessary power from an external power source.

Moreover, the hearing aid charger 200 may also be inserted into the receiving cavity 11 through alternative orientations. For example, the utility platform 31 may be detachably attached on the top surface 12 of the main casing so that a user may be able to detach the utility platform 31 from the main casing 10 and insert the hearing aid charger 200 from a top side of the main casing 10. The hearing aid charger 200 may then be connected to the PCB 24. After insertion and properly connected, the user may attach the utility platform 31 back to the main casing 10. The charging and drying station may then work in the manner described above.

Figure 5:
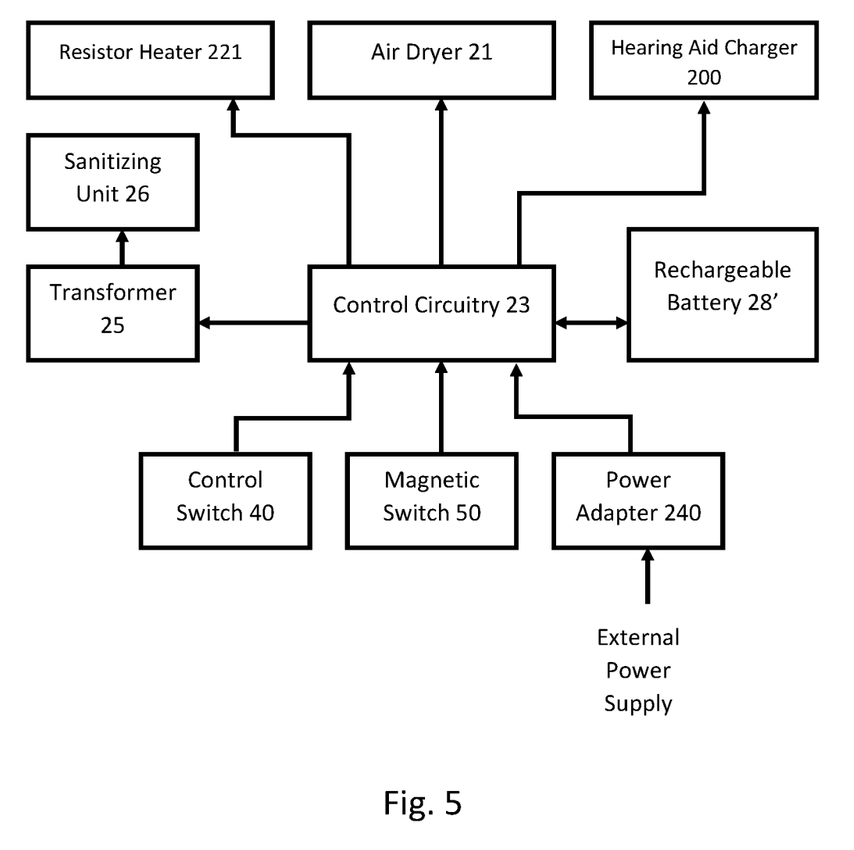
FIG. 5 is a schematic block diagram of the charging and drying station for a hearing aid device according to a first alternative mode of the first preferred embodiment of the present invention.

Referring to FIG. 5 of the drawings, a first alternative mode of the charging and drying station according to the first preferred embodiment of the present invention is illustrated. The first alternative mode is identical to the first preferred embodiment described above, except the drying arrangement 20 may further comprise a rechargeable battery 28' received in the receiving cavity 11 of the main casing 10 and electrically connected to the control circuitry 23 on the PCB 24 such that the entire drying and charging station may be powered from this rechargeable battery 28' when external power supply is not available. This rechargeable battery 28' may be automatically recharged when external power source is connected to the PCB 24, whether or not through the power adapter 240.

As a second alternative mode of the first preferred embodiment, the utility platform 31 may be integrally formed on the main casing 10. Moreover, the supporting tray 27 may also be integrally connected to the main casing 10 so that the main casing 10, the utility platform 31 and the supporting tray 27 may form a single piece of structure.

Referring to FIG. 6 to FIG. 10 of the drawings, a charging and drying station according a second preferred embodiment of the present invention is illustrated. As in the first preferred embodiment, the charging and drying station may be primarily for use with a hearing aid charger 200 having at least one charging terminal 201 to charge at least one hearing aid device 100. The hearing aid charger 200 may have a built-in rechargeable battery for charging the hearing aid device 100. In this second preferred embodiment, the charger accommodation arrangement 30 and the main casing 10 as described above may be structurally combined and modified. Thus, the charging and dryer station in the second preferred embodiment may comprise a main casing 10" and a drying arrangement 20".

Figure 6:
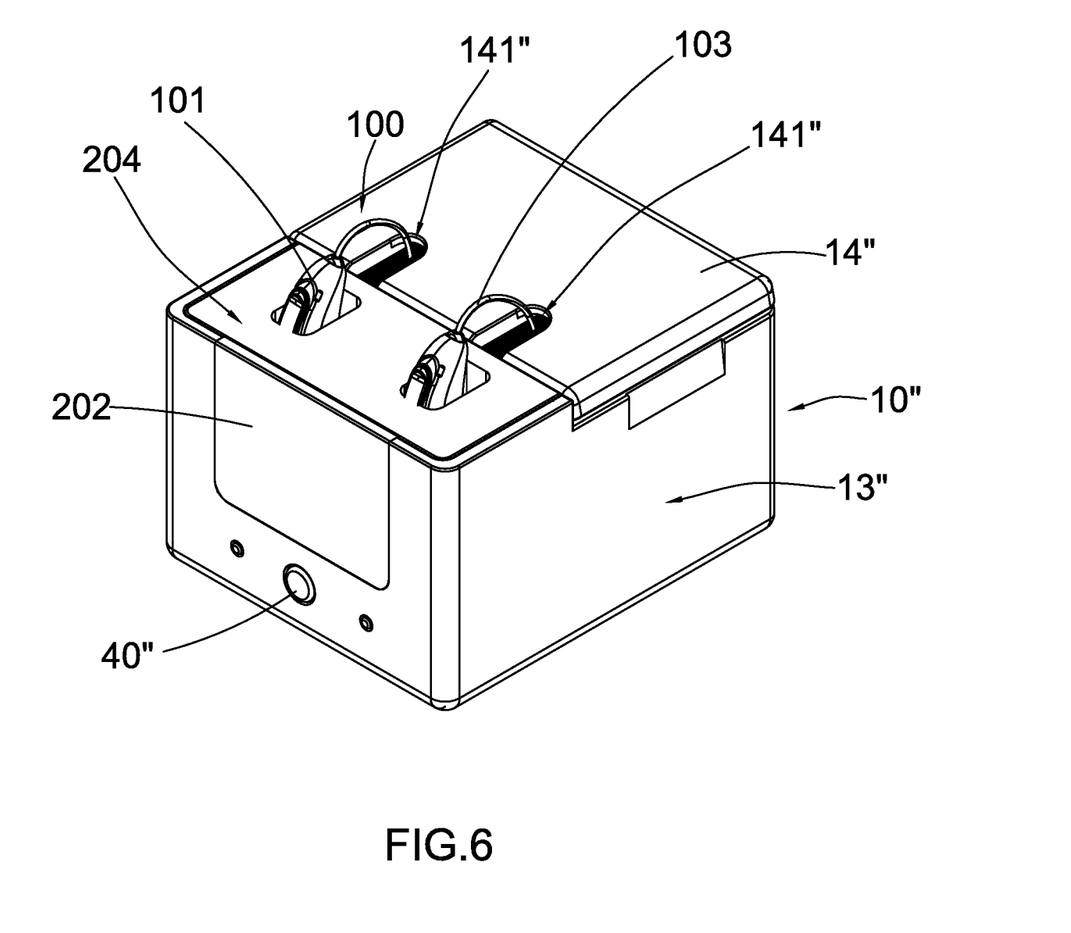
FIG. 6 is a perspective view of the charging and drying station for a hearing aid device according to a second preferred embodiment of the present invention, illustrating a covering member is closed.
Figure 7:
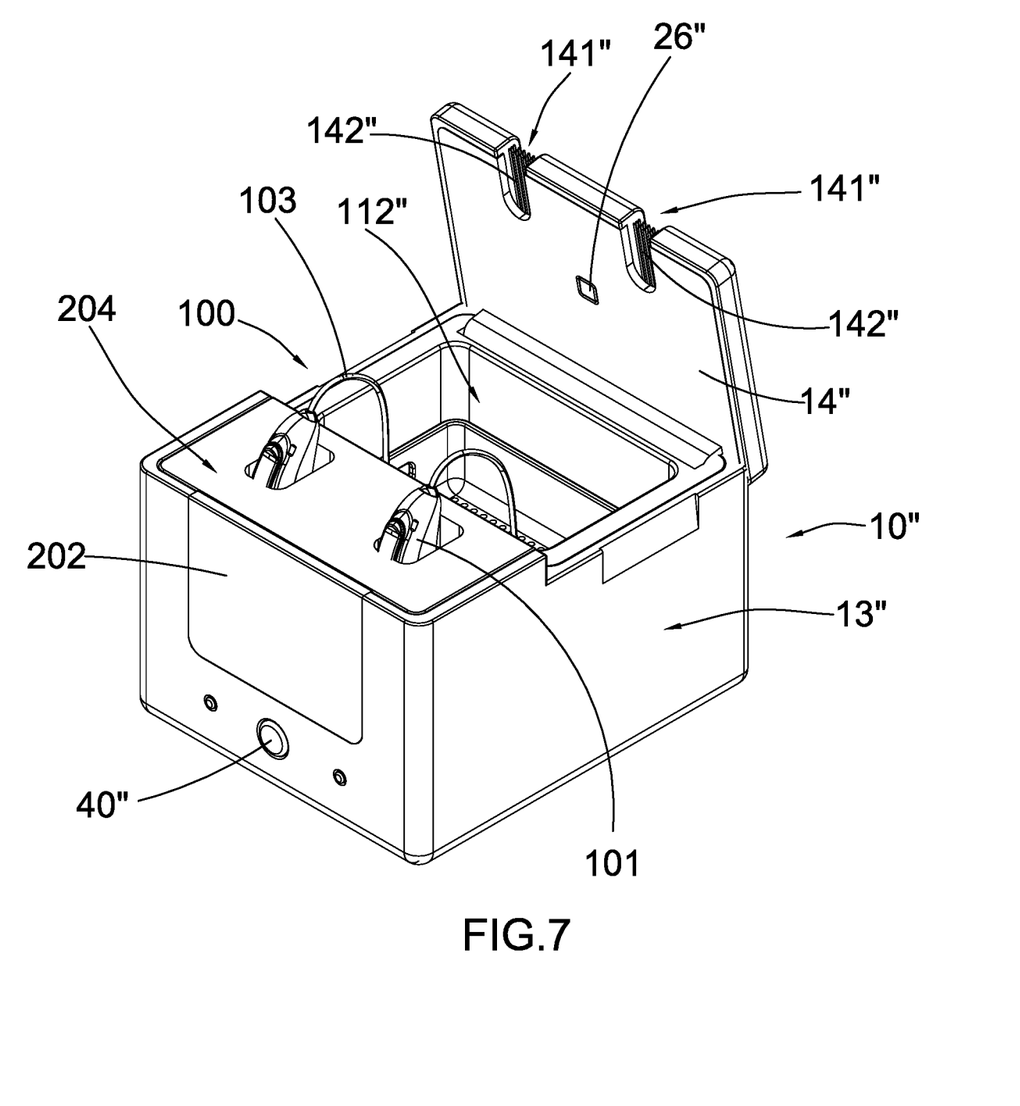
FIG. 7 is a perspective view of the charging and drying station for a hearing aid device according to the second preferred embodiment of the present invention, illustrating a covering member is opened.
Figure 8:
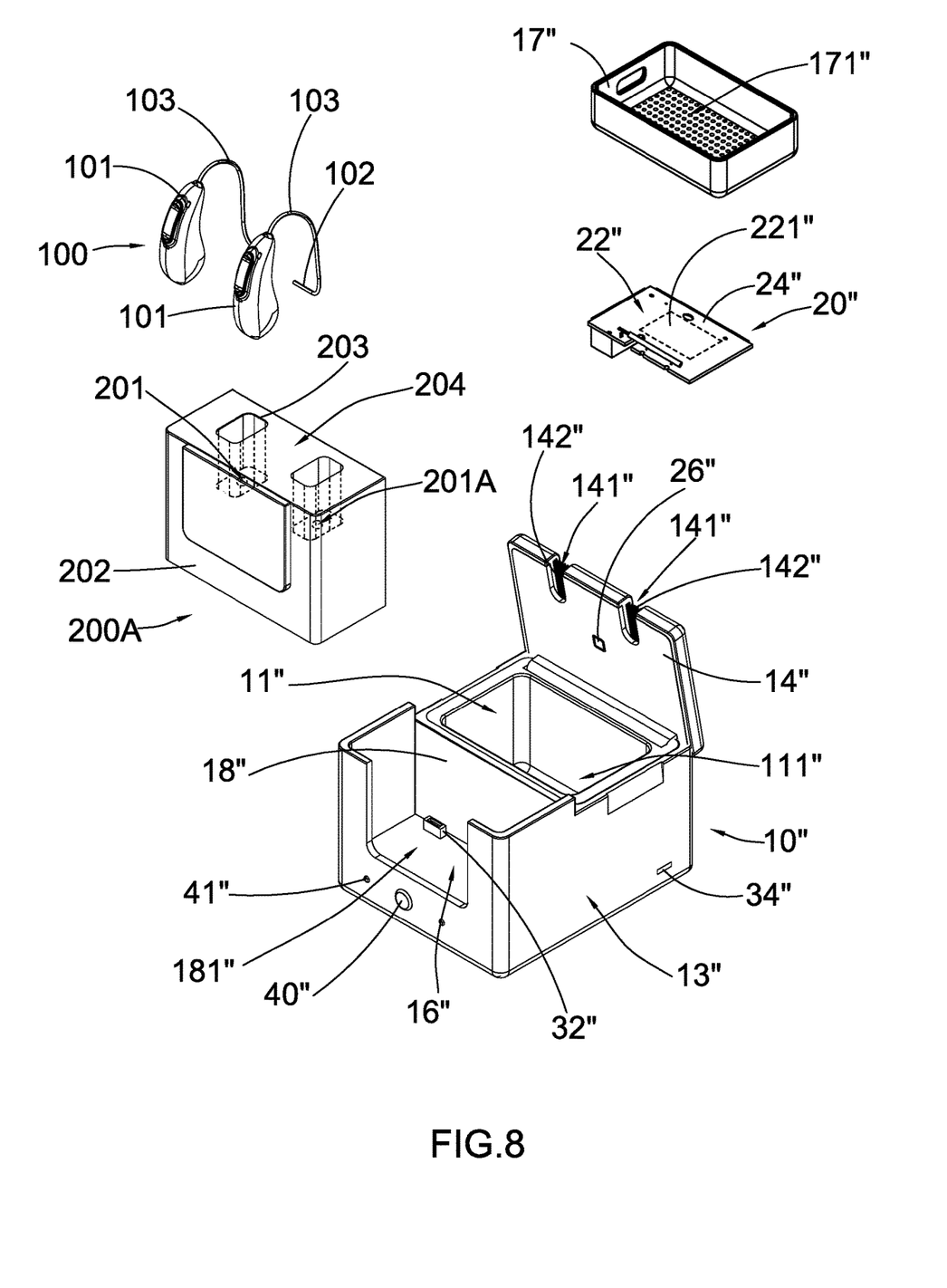
FIG. 8 is an exploded perspective view of the charging and drying station for a hearing aid device according to the second preferred embodiment of the present invention.

The main casing 10" may have a receiving cavity 11" and a charger accommodating cavity 16". The main casing 10" may further comprise a drying platform 17" provided in the receiving cavity 11" to divide the receiving cavity 11" into a supporting compartment 111" and a drying compartment 112". The drying compartment 112" may be formed above the supporting compartment 111'. The supporting compartment 111" may be formed underneath the drying platform 17" and may be invisible and protected from ambient environment.

Figure 10:
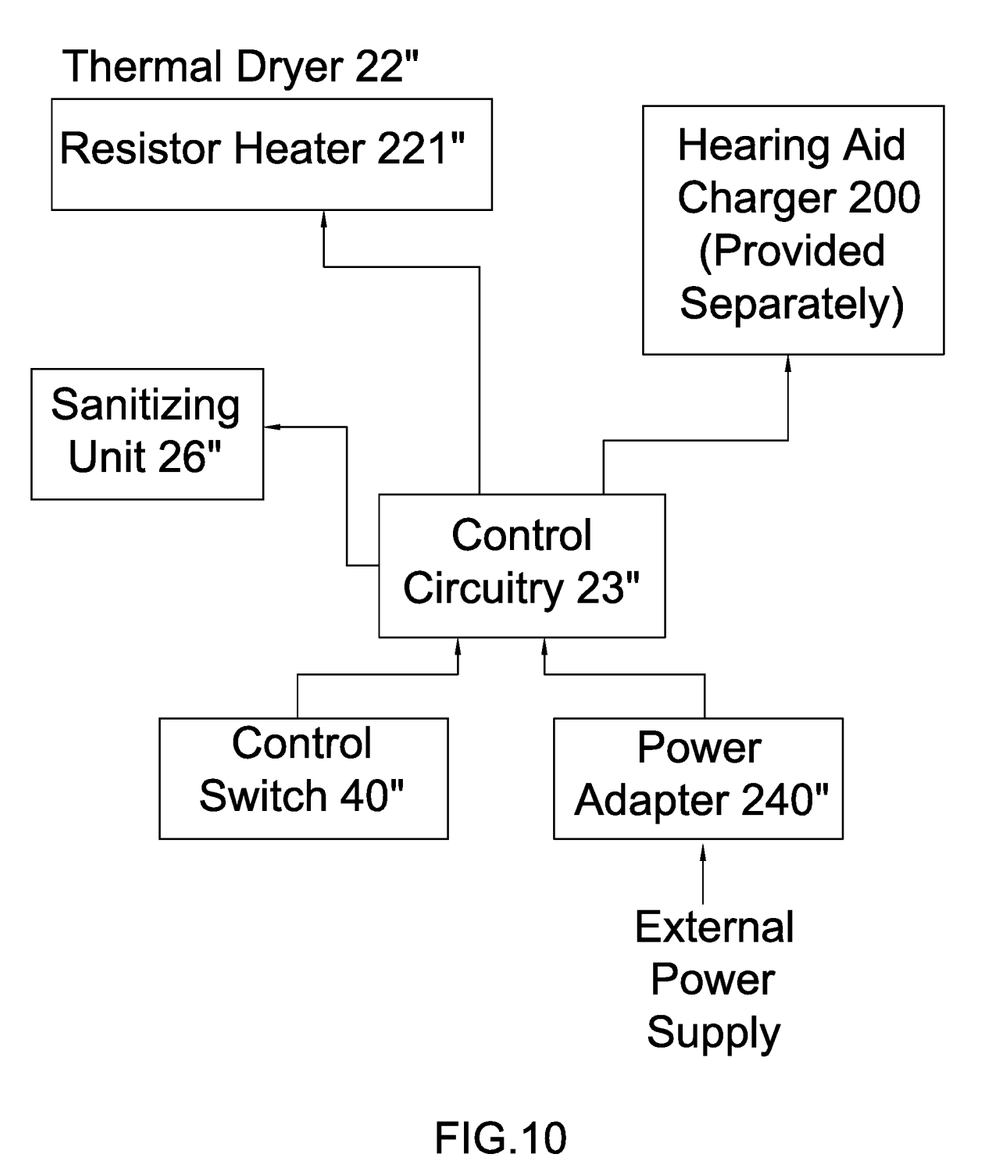
FIG. 10 is a schematic block diagram of the charging and drying station for a hearing aid device according to the second preferred embodiment of the present invention.

The drying arrangement 20" may be supported in the main casing 10" and may be accommodated in the receiving cavity 11". The drying arrangement 20" may comprise a thermal dryer 22" provided in the receiving cavity 11" for drying the hearing aid device 100.

Figure 9:
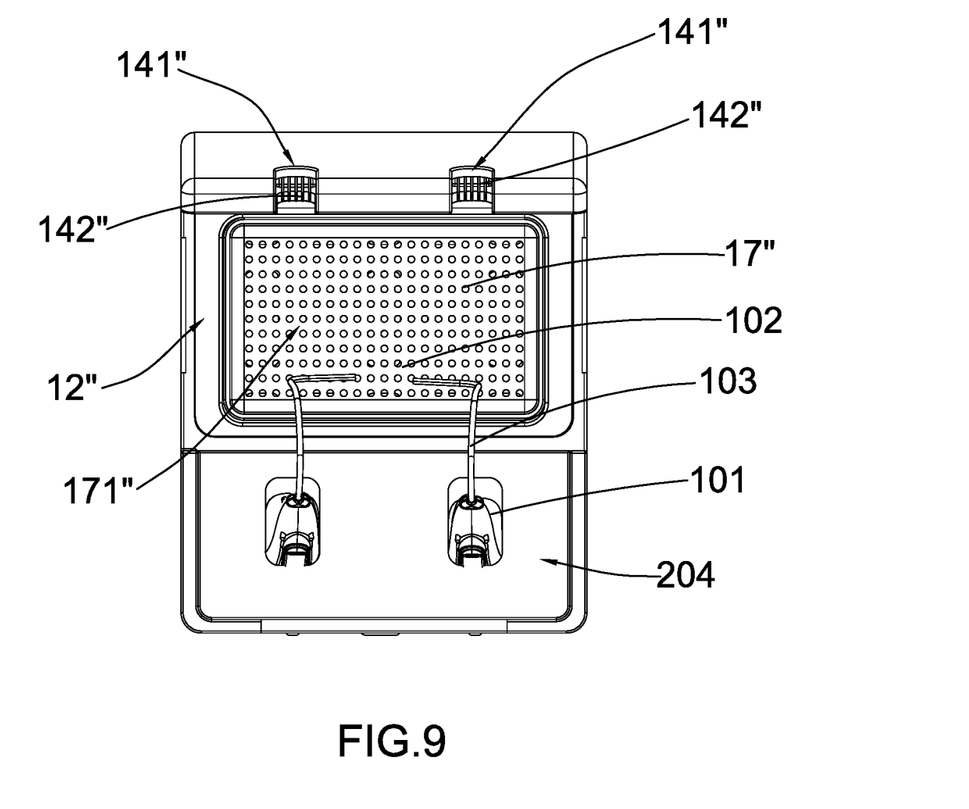
FIG. 9 is a plan view of the charging and drying station for a hearing aid device according to the second preferred embodiment of the present invention.

The charger accommodating cavity 16" formed in the main casing 10" may be shaped to fittedly accommodate the hearing aid charger 200 in a detachable manner, so that the hearing aid device 100 may be capable of being disposed on the hearing aid charger 200 for being simultaneously recharged and dried by the hearing aid charger 200 and the drying arrangement 20" respectively as shown in FIG. 9 of the drawings.

According to the second preferred embodiment of the present invention, the charging and drying station may be primarily for use with a predetermined hearing aid charger 200 having at least one charging terminal 201. The hearing aid charger 200 may be a leading hearing aid charger in the market and does not form part of the present invention. The size and shape of this hearing aid charger 200 may be utilized to design the size and shape of the charger accommodating cavity 16".

FIG. 8 illustrates one predetermined type of hearing aid charger 200 in which it may comprise a charger body 202, a plurality of charging adapters 203 provided on a top surface 204 of the charger body 202, wherein each of the charging adapters 203 may have a charging terminal 201 provided thereon. The housings 101 of the hearing aid devices 100 may be securely disposed on the charging adapters 203 respectively for charging of the hearing aid devices 100.

FIG. 6 illustrates charging of two hearing aid devices 100 by a hearing aid charger 200. Each of the hearing aid devices 100 may comprise a housing 101, an earplug 102, and an extension cord 103 extended between the housing 101 and the earplug 102. The earplug 102 and the extension cord 103 may be made of flexible and soft material while the housing 101 may be made of rigid material. Electronic components may be received in the housing 101. The two hearing aid devices 100 may be conventional and well-known in the art and do not form part of the present invention.

The main casing 10" may have a top surface 12" and a boundary surface 13". The charging and drying station may further comprise a covering member 14" movably mounted on the main casing 10" for selectively covering at least the drying compartment 112".

The receiving cavity 11" and the charger accommodating cavity 16" may be separated or divided by a partition 18" extended in the main casing 10". Thus, the receiving cavity 11" may be formed on one side (such as a rear side) of the partition 18" while the charger accommodating cavity 16" may be formed on another side (such as a front side) of the partition 18".

As shown in FIG. 6 to FIG. 7 of the drawings, the main casing 10" may further have a front opening 181" communicating the charger accommodating cavity 16" with an exterior of the main casing 10". The front opening 181" may provide a window for allowing a user to observe a charging operation of the hearing aid charger 200. For example, a user may be able to visually observe a charging light provided on the hearing aid charger 200 when the hearing aid charger 200 is detachably accommodated in the charger accommodating cavity 16".

The drying arrangement 20" may further comprise a control circuitry 23" implemented on a Printed Circuit Board (PCB 24"). The PCB 24" may be securely supported in the supporting compartment 111' of the receiving cavity 11'. The PCB 24" may be electrically connected to an external power source, preferably through a power adapter 240", for acquiring electricity for the entire charging and drying station.

The drying arrangement 20" may further comprise a sanitizing unit 26" supported in the drying compartment 112" of the receiving cavity 11" and electrically connected to the PCB 24" and the control circuitry 23" for sanitizing the hearing aid device 100 when it is disposed on the drying platform 17". The sanitizing unit 26" may be configured as an ultra-violet (UV) light mounted on the covering member 14" so that when the covering member 14" is pivotally moved to cover the drying compartment 112", the sanitizing unit 26" may be arranged to generate ultra-violet radiation primarily toward the drying platform 17" for sanitizing the hearing aid devices 100 disposed thereon.

The charging and drying station of the present invention may be configured to allow a user to dry and charge his hearing aid device 100 simultaneously. The drying platform 17" may have a plurality of through dryer slots 171", wherein the supporting compartment 111" may communicate with the drying compartment 112" through the through dryer slot 171". The drying platform 17" may be shaped and sized to have an indention for supporting the earplugs 102 of the hearing aid devices 100, as shown in FIG. 9 of the drawings.

The drying platform 17" may be shaped and sized to accommodate at least the earplugs 102 of the hearing aid device 100 so that the earplugs 102 may rest on the drying platform 17" for being dried by the drying arrangement 20". According to the second preferred embodiment of the present invention, the drying arrangement 20" may comprise the thermal dryer 22" which may comprise at least one resistor heater 221" mounted in the PCB 24". The resistor heater 221" may be arranged to generate heat in the drying compartment 112". Heated air may be circulated from the thermal dryer 22" to the earplug 102 through the through dryer slots 171".

It is worth mentioning that the drying platform 17" may be integrally formed on the main casing 10" so that the drying platform 17" and the main casing 10" may form a one-piece structure. Alternatively, the drying platform 17" may be a separate component and mounted in the receiving cavity 11" of the main casing 10".

The main casing 10" may further comprise a first power port 32" provided in the charger accommodating cavity 16" and electrically connected to the PCB 24", wherein the hearing aid charger 200 may be electrically connected to the first power port 32" when it is accommodated in the charger accommodating cavity 16". The first power port 32" may be configured as a USB power port such as a USB C-type power port. The power supplied to the hearing aid charger 200 through the first power port 32" may be used to recharge the hearing aid charger 200 and/or the hearing aid device 100.

On the other hand, the main casing 10" may further comprise a second power port 34" provided thereon and electrically connected to the PCB 24" preferably through the power adapter 240" which may be built-in in the main casing 10". The second power port 34" may be arranged to electrically connect to an external power source so as to acquire power to charge the hearing aid charger 200 and/or to operate the drying arrangement 20".

Thus, when the hearing aid charger 200 is properly accommodated in the charger accommodating cavity 16", a user may then charge the hearing aid devices 100 by connecting the hearing aid devices 100 to the charging adapters 203 respectively while placing the hearing aid charger 200 in the charger accommodating cavity 16". Moreover, the earplugs 102 may extend to the drying platform 17" so as to allow the drying arrangement 20" to dry the earplugs 102.

The covering member 14" may be pivotally mounted to the main casing 10" and may be arranged to pivotally move to cover the drying compartment 112". The covering member 14" may have a plurality of (but at least one) passage slots 141" for allowing the extension cords 103 to pass through. In other words, when the hearing aid charger 200 is properly accommodated in the charger accommodating cavity 16", and the hearing aid devices 100 are connected to the hearing aid charger 200, and the earplugs 102 of the hearing aid devices 100 may be supported on the drying platform 17". When the covering member 14" is moved to close the drying compartment 112", the extension cords 103 may pass through the passage slots 141" respectively so as to allow the covering member 14" to properly cover the drying compartment 112". When the covering member 14"

is moved to close the drying compartment 112", the drying compartment 112" may only communicate with the ambient environment through the passage slots 141".

Furthermore, the covering member 14" may further comprise a plurality of bristles 142" mounted in the passage slots 141". The bristles 142" may prevent unwanted materials from entering the drying compartment 112" but at the same time allow communication or ventilation between the drying compartment 112" and ambient environment.

The charging and drying station may further comprise a control switch 40" provided on the main casing 10" and electrically connected to the control circuitry 23", wherein a user may control an operation of the charging and drying station through actuating the control switch 40".

The operation of the present invention is as follows: the charging and drying station in the second preferred embodiment of the present invention does not come with a hearing aid charger 200. Rather, the present invention is for accommodating a predetermined hearing aid charger 200 which is adapted to charge a hearing aid device 100. The charging and drying station of the present invention may be sized and shaped to simultaneously dry and charge two hearing aid devices 100. Thus, a user may insert the hearing aid charger 200 in the charger accommodating cavity 16" and connect the hearing aid devices 100 to the hearing aid charger 200. The earplugs 102 may then be disposed on the drying platform 17". After that, the user may close the covering member 14" enclose the drying compartment 112".

The user may then turn on the thermal dryer 22" and/or the sanitizing unit 26" by operating on the control switch 40". Thus, the hearing aid devices 100 may be recharged and dried simultaneously by using the present invention. The temperature within the drying compartment 112" may be raised to a predetermined level while other parts of the hearing aid devices 100 (such as the housings 101) and the hearing aid charger 200 may be kept and maintained at room temperature.

Figure 11:
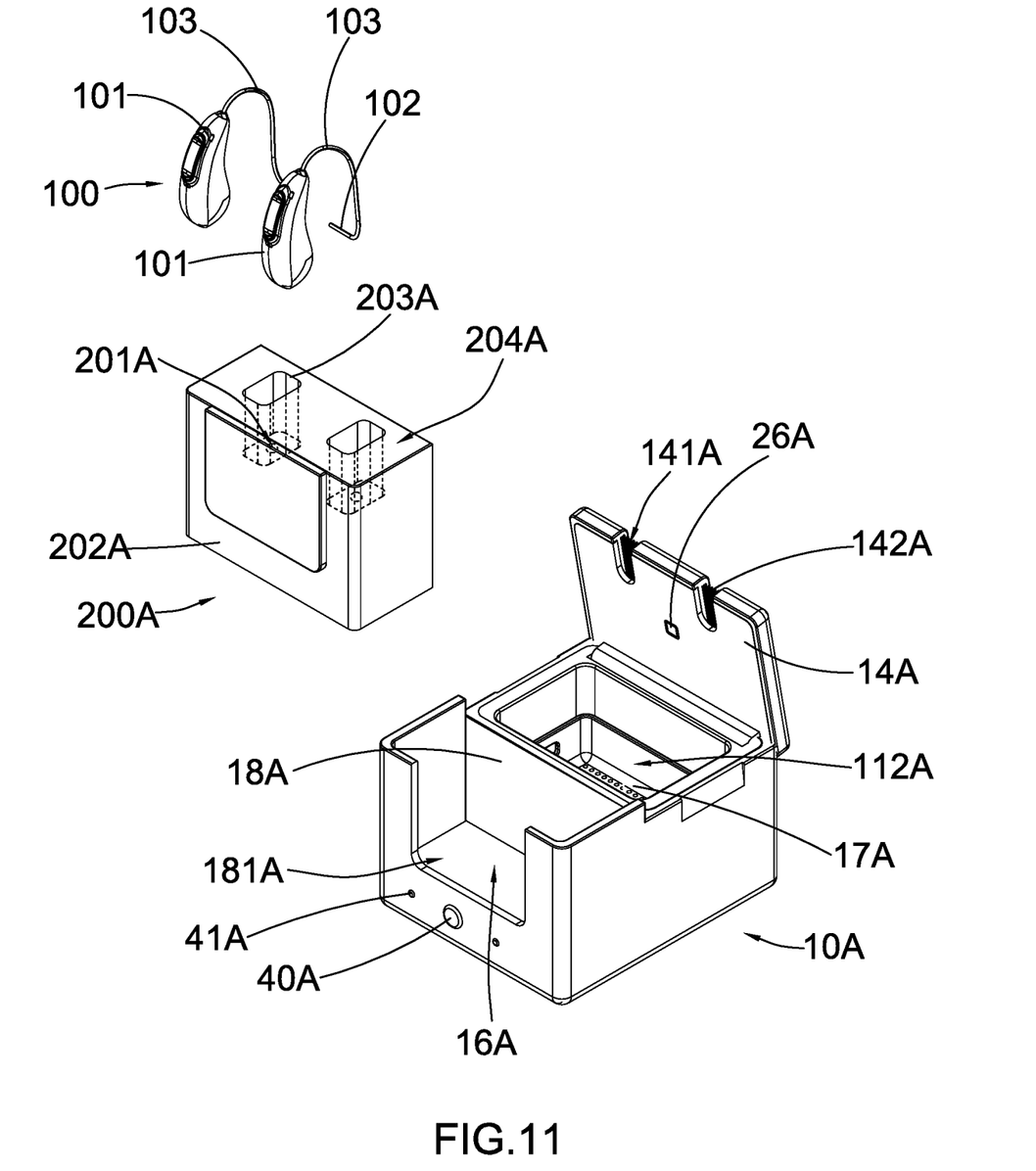
FIG. 11 is a perspective view of the charging and drying station for a hearing aid device according to a third preferred embodiment of the present invention.
Figure 12:
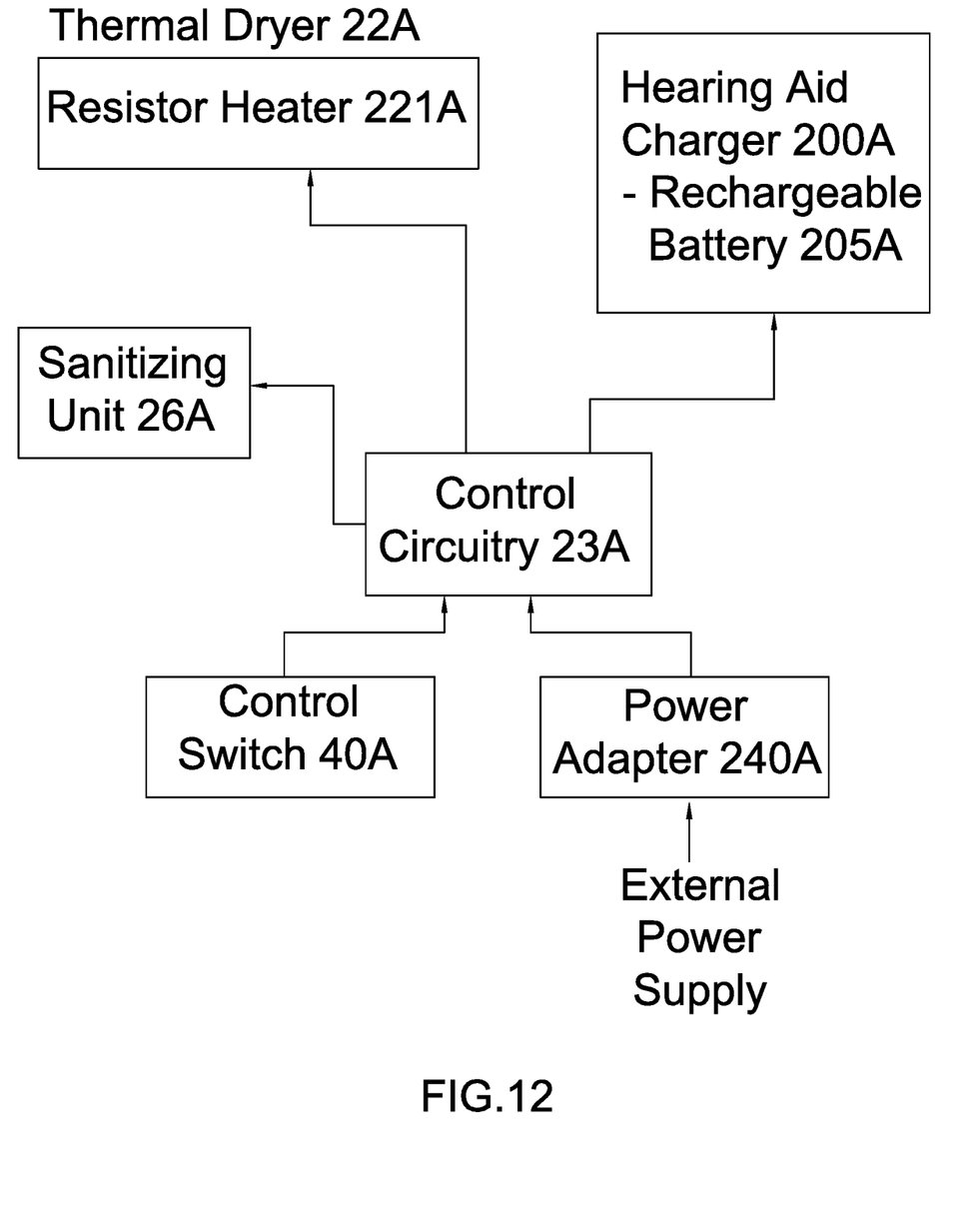
FIG. 12 is a schematic block diagram of the charging and drying station for a hearing aid device according to the third preferred embodiment of the present invention.

Referring to FIG. 11 to FIG. 12 of the drawings, a charging and drying station in according to a third preferred embodiment of the present invention is illustrated. The third preferred embodiment is identical to the second preferred embodiment, except that the hearing aid charger 200A is provided in the main casing 10A as part of the present invention. The hearing aid charger 200A, however, is selectively detachable from the main casing 10A. The difference between the second preferred embodiment and the third preferred embodiment is that in the second preferred embodiment, the hearing aid charger 200 is not part of the invention so that a user may need to purchase the hearing aid charger 200 separately. The charger accommodating cavity 16" may be specifically sized and shaped during manufacturing process for fitting different types of existing or leading hearing aid chargers 200.

In contrast, in the third preferred embodiment of the present invention, the hearing aid charger 200A is included as part of the invention so that a user does not need to separately purchase one. The hearing aid charger 200A may be detachably attached on the main casing 10A in the charger accommodating cavity 16A.

Thus, the hearing aid charger 200A may have at least one charging terminal 201A to charge at least one hearing aid device 100. Moreover, the hearing aid charger 200A may comprise a charger body 202A, a plurality of charging adapters 203A provided on a top surface 204A of the charger body 202A, wherein each of the charging adapters 203A may have the charging terminal 201A provided thereon. The housings 101 of the hearing aid devices 100 may be securely disposed on the charging adapters 203A respectively for charging of the hearing aid devices 100. The hearing aid charger 200A may therefore comprise a rechargeable battery 205A received in the charger body 202A and electrically connected to the charging adapters 203A and the charging terminal 201A.

Other than the hearing aid charger 200A, other components of the charging and drying station are identical to what has been disclosed in the second preferred embodiment. Moreover, the control switch 40A and the indicator lights 41A may be provided on the hearing aid charger 200A instead of the main casing 10A. A user may be able to operate the control switch 40A and observe the indicator lights 41A through the front opening 181A.

The operation of the present invention is as follows: the charging and drying station in the third preferred embodiment of the present invention does come with a hearing aid charger 200A. The heading aid charger 200A may be detachably attached in the charger accommodating cavity 16A. The charging and drying station of the present invention may be sized and shaped to simultaneously dry and charge two hearing aid devices 100. Thus, a user may attach the hearing aid charger 200A in the charger accommodating cavity 16A and connect the hearing aid devices 100 to the hearing aid charger 200. The earplugs 102 may then be disposed on the drying platform 17A. After that, the user may close the covering member 14A enclose the drying compartment 112A. The drying compartment 112A and the charger accommodating cavity 16A may be separated by the partition 18A.

The user may then turn on the thermal dryer 22A, the resistor heater 221A and/or the sanitizing unit 26A by operating on the control switch 40". Thus, the hearing aid devices 100 may be recharged and dried simultaneously by using the present invention. The temperature within the drying compartment 112A may be raised to a predetermined level while other parts of the hearing aid devices 100 (such as the housings 101) and the hearing aid charger 200A may be kept and maintained at room temperature.

Furthermore, the bristles 142A provided in the passage slots 141A may prevent unwanted materials from entering the drying compartment 112A but at the same time allow communication or ventilation between the drying compartment 112" and ambient environment.

As in the second preferred embodiment, all operations of the charging and drying station may be centrally controlled and operated by the control circuitry 23A. Thus, the control circuitry 23A may be electrically connected to the drying arrangement 20A and the thermal dryer 22A and the hearing aid charger 200A and the rechargeable battery 205A. The charging and drying station may also be connected to an external power source through a power adapter 240A.

The present invention, while illustrated and described in terms of a preferred embodiment and several alternatives, is not limited to the particular description contained in this specification. Additional alternative or equivalent components could also be used to practice the present invention.

What is claimed is:

1. A charging and drying station for a hearing aid charger having a charging terminal to charge a hearing aid device which comprises a housing, an earplug and an extension cord connecting said housing and said earplug, said charging and drying station comprising:

a main casing having a receiving cavity and a charger accommodating cavity, said main casing further comprising a drying platform provided in said receiving cavity to divide said receiving cavity into a supporting compartment and a drying compartment on underneath and above said drying platform respectively; and a drying arrangement, which comprises a thermal dryer provided in said supporting compartment of said receiving cavity for generating heat in said drying platform, wherein said charger accommodating cavity is shaped and sized to fittedly accommodate said hearing aid charger in a detachable manner, so that said housing of said hearing aid device is capable of being disposed on said hearing aid charger while said earplug of said hearing aid device is arranged to be disposed on said drying platform so that said hearing aid device is simultaneously recharged and dried by said hearing aid charger and said drying arrangement respectively.

2. The charging and drying station, as recited in claim 1, wherein main casing further has a top surface and a boundary surface, a partition dividing said receiving cavity and said charger accommodating cavity on two sides of said partition respectively.

3. The charging and drying station, as recited in claim 2, wherein said main casing further has a front opening communicating said charger accommodating cavity with an exterior of said main casing.

4. The charging and drying station, as recited in claim 3, further comprising a covering member movably mounted on said main casing for selectively covering at least said drying compartment of said main casing.

5. The charging and drying station, as recited in claim 4, wherein said drying arrangement further comprises a printed circuit board received in said supporting compartment of said receiving cavity, and a control circuitry implemented on said printed circuit board for controlling said drying arrangement.

6. The charging and drying station, as recited in claim 5, wherein said drying arrangement further comprises a sanitizing unit supported in said drying compartment of said receiving cavity and electrically connected to said printed circuit board and said control circuitry for sanitizing at least said earplug of said hearing aid device when said earplug is disposed on said drying platform and when said covering member is moved to close said drying compartment.

7. The charging and drying station, as recited in claim 6, wherein said covering member further has at least one passage slot for allowing said extension cord to pass through when said covering member is moved to close said drying compartment.

8. The charging and drying station, as recited in claim 7, wherein said covering member further comprises a plurality of bristles mounted in said passage slots for preventing unwanted materials from entering said drying compartment and at the same time allowing communication between said drying compartment and ambient environment.

9. A charging and drying station for a hearing aid device which comprises a housing, an earplug and an extension cord connecting said housing and said earplug, said charging and drying station comprising:

a hearing aid charger which comprises a charger body, at least one charging adapter provided on said charger body, at least one charging terminal provided on said charging adapter, and a rechargeable battery provided in said charger body and electrically connected to said charging terminal;

a main casing having a receiving cavity and a charger accommodating cavity, said main casing further comprising a drying platform provided in said receiving cavity to divide said receiving cavity into a supporting compartment and a drying compartment on underneath and above said drying platform respectively, said charger accommodating cavity being shaped and sized to fittedly accommodate said hearing aid charger; and a drying arrangement which comprises a thermal dryer provided in said supporting compartment of said receiving cavity for generating heat in said drying platform, said hearing aid charging being detachably attached on said main casing in said charger accommodating cavity, so that said housing of said hearing aid device is capable of being disposed on said hearing aid charger while said earplug of said hearing aid device is arranged to be disposed on said drying platform so as to allow said hearing aid device is capable of being simultaneously recharged and dried by said hearing aid charger and said drying arrangement respectively.

10. The charging and drying station, as recited in claim 9, wherein main casing further has a top surface and a boundary surface, a partition dividing said receiving cavity and said charger accommodating cavity on two sides of said partition respectively.

11. The charging and drying station, as recited in claim 10, wherein said main casing further has a front opening communicating said charger accommodating cavity with an exterior of said main casing.

12. The charging and drying station, as recited in claim 11, further comprising a covering member movably mounted on said main casing for selectively covering at least said drying compartment of said main casing.

13. The charging and drying station, as recited in claim 12, wherein said drying arrangement further comprises a printed circuit board received in said supporting compartment of said receiving cavity, and a control circuitry implemented on said printed circuit board for controlling said drying arrangement.

14. The charging and drying station, as recited in claim 13, wherein said drying arrangement further comprises a sanitizing unit supported in said drying compartment of said receiving cavity and electrically connected to said printed circuit board and said control circuitry for sanitizing at least said earplug of said hearing aid device when said earplug is disposed on said drying platform and when said covering member is moved to close said drying compartment.

15. The charging and drying station, as recited in claim 14, wherein said covering member further has at least one passage slot for allowing said extension cord to pass through when said covering member is moved to close said drying compartment.

* * * * *